United States Patent [19]

Hunziker

[11] Patent Number: 5,270,300
[45] Date of Patent: Dec. 14, 1993

[54] METHODS AND COMPOSITIONS FOR THE TREATMENT AND REPAIR OF DEFECTS OR LESIONS IN CARTILAGE OR BONE

[75] Inventor: Ernst B. Hunziker, Riedholz, Switzerland

[73] Assignee: Robert Francis Shaw, San Francisco, Calif.

[21] Appl. No.: 756,164

[22] Filed: Sep. 6, 1991

[51] Int. Cl.$^5$ .................. C07K 15/06; C09H 3/02; A61K 37/22; A61K 37/24; A61K 37/36

[52] U.S. Cl. .................. 514/12; 424/422; 424/423; 424/424; 424/425; 424/426; 424/450; 424/484; 424/489; 424/499; 514/2; 514/8; 514/56; 514/944; 514/965; 530/350; 530/351; 530/353; 530/354; 530/356; 530/840

[58] Field of Search .................. 514/12, 2, 8, 56, 944, 514/965; 424/422, 423, 424, 425, 426, 450, 484, 489, 499; 530/350, 351, 353, 354, 356, 840

[56] References Cited

U.S. PATENT DOCUMENTS

| | | | |
|---|---|---|---|
| 3,966,908 | 6/1976 | Balassa | 424/95 |
| 4,346,709 | 8/1982 | Schmidtt | 128/260 |
| 4,418,691 | 12/1983 | Yannas et al. | 128/156 |
| 4,563,350 | 1/1986 | Nathan | 514/21 |
| 4,604,234 | 8/1986 | Fujii et al. | 514/2 |
| 4,609,551 | 9/1986 | Caplan et al. | 424/95 |
| 4,627,982 | 12/1986 | Seyedin et al. | 424/95 |
| 4,638,045 | 1/1987 | Kohn et al. | 530/323 |
| 4,642,120 | 2/1987 | Nevo et al. | 623/16 |
| 4,774,228 | 9/1988 | Seyedin et al. | 514/21 |
| 4,774,322 | 9/1988 | Seyedin et al. | 530/353 |
| 4,785,079 | 11/1988 | Gospodarowicz et al. | 530/399 |
| 4,795,804 | 1/1989 | Urist | 530/350 |
| 4,804,744 | 2/1989 | Sen | 530/350 |
| 4,810,691 | 3/1989 | Seyedin et al. | 514/2 |
| 4,839,215 | 6/1989 | Starling et al. | 428/131 |
| 4,843,063 | 6/1989 | Seyedin et al. | 514/2 |
| 4,846,835 | 7/1989 | Grande | 623/11 |
| 4,877,864 | 10/1989 | Wang et al. | 530/324 |
| 4,886,747 | 12/1989 | Derynck et al. | 435/69.4 |
| 4,888,366 | 12/1989 | Chu et al. | 523/115 |
| 4,917,893 | 4/1990 | Okada et al. | 424/423 |
| 4,944,948 | 7/1990 | Uster et al. | 424/450 |
| 4,950,483 | 8/1990 | Ksander et al. | 424/422 |
| 4,952,403 | 8/1990 | Vallee et al. | 424/422 |
| 4,952,404 | 8/1990 | Vallee et al. | 424/422 |
| 4,975,526 | 12/1990 | Kuberasampath et al. | 530/350 |
| 5,158,934 | 10/1992 | Ammann et al. | 514/12 |
| 5,206,023 | 4/1993 | Hunziker | 424/422 |

FOREIGN PATENT DOCUMENTS

128849A1 12/1984 European Pat. Off. .
293785A2 12/1988 European Pat. Off. .

(List continued on next page.)

OTHER PUBLICATIONS

Ksander et al., "Exogenous Transforming Growth Factor-Beta 2 Enhances Connective Tissue Formation and Wound Strength in Guinea Pig Dermal Wounds Healing by Secondary Intent," *Ann. Surg.*, 211, pp. 288-294 (Philadelphia: Mar. 1990).

(List continued on next page.)

*Primary Examiner*—Ronald W. Griffin
*Attorney, Agent, or Firm*—Edward F. Mullowney; Jane A. Massaro

[57] ABSTRACT

Methods and compositions are provided for the treatment and repair of defects in the cartilage or bone of humans and other animals as in full-thickness defects in joints. The defect in bone is filled with a matrix having pores large enough to allow cells to populate the matrix and to form blood vessels. The matrix filling the bone defect contains an angiogenic factor and also contains an osteogenic factor in an appropriate delivery system. To induce cartilage formation, a defect in cartilage is filled with a matrix having pores sufficiently large to allow cartilage repair cells to populate the matrix. The matrix filling the defect in cartilage contains a proliferation agent and also contains a transforming factor in an appropriate delivery system. The matrix may also contain a chemotactic agent to attract cartilage repair cells. In a full-thickness defect, the defect sites in bone and cartilage are separated from each other by a membrane, which is sealed to the cartilage-bone-junction and which prevents blood vessels and associated cells from penetrating from one site to the other.

26 Claims, No Drawings

FOREIGN PATENT DOCUMENTS

| | | |
|---|---|---|
| 0295721A2 | 12/1988 | European Pat. Off. |
| 0308238A1 | 3/1989 | European Pat. Off. |
| 0361896A3 | 4/1990 | European Pat. Off. |
| 0361896A2 | 4/1990 | European Pat. Off. |
| 394152A1 | 4/1990 | European Pat. Off. |
| 374044A2 | 6/1990 | European Pat. Off. |
| 0375127A1 | 6/1990 | European Pat. Off. |
| 376785A2 | 7/1990 | European Pat. Off. |
| 167263B1 | 8/1990 | European Pat. Off. |
| WO86/00526 | 1/1986 | PCT Int'l Appl. |
| WO90/00526 | 1/1986 | PCT Int'l Appl. |
| 8607595 | 12/1986 | PCT Int'l Appl. |
| 8800205 | 1/1988 | PCT Int'l Appl. |
| 8805788 | 8/1988 | PCT Int'l Appl. |
| 8904173 | 5/1989 | PCT Int'l Appl. |
| WO89/04646 | 6/1989 | PCT Int'l Appl. |
| 8907425 | 8/1989 | PCT Int'l Appl. |
| 8907613 | 8/1989 | PCT Int'l Appl. |
| 8909787 | 10/1989 | PCT Int'l Appl. |
| 8909788 | 10/1989 | PCT Int'l Appl. |
| 8912101 | 12/1989 | PCT Int'l Appl. |
| 9000060 | 1/1990 | PCT Int'l Appl. |
| 9003733 | 4/1990 | PCT Int'l Appl. |
| WO90/05755 | 5/1990 | PCT Int'l Appl. |
| WO90/06767 | 6/1990 | PCT Int'l Appl. |
| 9009166 | 8/1990 | PCT Int'l Appl. |
| WO90/09783 | 9/1990 | PCT Int'l Appl. |
| 9009783 | 9/1990 | PCT Int'l Appl. |
| 9010017 | 9/1990 | PCT Int'l Appl. |
| 9010018 | 9/1990 | PCT Int'l Appl. |
| 9013317 | 11/1990 | PCT Int'l Appl. |
| 9104267 | 4/1991 | PCT Int'l Appl. |
| WO92/13565 | 8/1992 | PCT Int'l Appl. |

OTHER PUBLICATIONS

Andrews, E. L., "Next: Artificial Bone to Repair Fractures," *New York Times*, p. D10 (Oct. 24, 1990).

Burgess, A. W., "Hemopoietic growth factors: structure and receptor interactions," In *Growth factors in biology and medicine*, pp. 148-168 (London: Pitman, 1985).

Callahan, M. et al., "The PDGF-inducible 'competence genes': intracellular mediators of the mitogenic response," In *Growth factors in biology and medicine*, pp. 87-97 (London: Pitman, 1985).

Cheifetz, S. et al., "The Transforming Growth Factor-β System, a Complex Pattern of Cross-Reactive Ligands and Receptors," *Cell*, 48, pp. 409-415 (Feb. 13, 1987).

Cuevas, P. et al., "Basic Fibroblast Growth Factor (FGF) Promotes Cartilage Repair In Vivo," *Biochem. Biophys, Res. Commun.*, 156, pp. 611-618 (Oct. 31, 1988).

Davidson, J. M., et al., "Accelerated Wound Repair, Cell Proliferation, and Collagen Accumulation are Produced by a Cartilage-derived Growth Factor," *J. Cell Biol.*, 100, pp. 1219-1227 (1985).

Dexter, T. M. et al., "The role of hemopoietic cell growth factor (interleukin 3) in the development of hemopoietic cells," In *Growth factors in biology and medicine*, pp. 129-147 (London: Pitman, 1985).

Dijke, P. et al., "Growth Factors For Wound Healing," *Biotech.*, 7, pp. 793-798 (Aug., 1989).

Folkman, J. et al., "Angiogenic Factors," *Science*, 235, pp. 442-447 (1987).

Gimenez-Gallego, G. et al., "Human Brain-Derived Acidic and Basic Fibroblast Growth Factors: Amino Terminal Sequences and Specific Mitogenic Activities," *Biochem. Biophys. Res. Commun.*, 135, pp. 541-548 (Mar. 13, 1986).

Gospodarowicz, D. et al., "Clonal growth of bovine vascular-endothelial cells: fibroblast growth factor as survival agent." *Proc. Natl. Acad. Sci. (USA)*, 73, pp. 4120-4124 (1976).

Hattori, T., "Experimental investigations of osteogenesis and chondrogenesis by implant of BMP-fibrin glue mixture," *Seikeigeka Gakkai Zasshi*, 64, pp. 824-834 (1990) (English Abstract).

Heller, J. et al., "Use of Bioerodible Polymers in Self-Regulated Drug Delivery Systems," In *Controlled Release Technology* pp. 172-187 (Washington, D.C.: American Chemical Society, 1987).

Huang, J. S. et al., "Role of growth factors in oncogenesis: growth factor-proto-oncogene pathways of mitogenesis," In *Growth factors in biology and medicine*, pp. 46-65 (London: Pitman, 1985).

Hutchinson, F. G. et al., "Design of biodegradable polymers for controlled release," In *Drug Delivery Systems*, pp. 106-119 (Chichester: Ellis Horwood, 1987).

Ignotz, R. A. et al., "Transforming Growth Factor-β Stimulates the Expression of Fibronectin and Collagen and Their Incorporation into the Extracellular Matrix," *J. Biol. Chem.*, 261, pp. 4337-4345 (Mar. 25, 1986).

Kim, S. et al., "Preparation of Multivesicular Lipo- (List continued on next page.)

OTHER PUBLICATIONS somes," *Biochim. Biophys. Acta*, 728, pp. 339-348 (1983).

Moore, A. R. et al., "The Chemotactic Properties of Cartilage Glycosaminoglycans for Polymer pronuclear Neutrophils," *Int. J. Tiss. Reac.*, XI pp. 301-307 (1989).

Postelthwaite, A. E. et al., "Stimulation of the Chemotactic Migration of Human Fibroblasts by Transforming Growth Factor $\beta$," *J. Exp. Med.*, 165, pp. 351-256 (Jan., 1987).

Ray, N. et al., "Implantable osmotically powered drug delivery systems," In *Drug Delivery Systems*, pp. 120-138 (Chichester: Ellis Horwood, 1987).

Rizzino, A., "Transforming Growth Factor-$\beta$: Multiple Effects on Cell Differentiation and Extracellular Matrices," *Develop. Biol.*, 130, pp. 411-422 (1988).

Roberts, A. B. et al., "The Transforming Factor-$\beta$s", In *Peptide Growth Factors and Their Receptors I*, pp. 419-472 (Berlin: Springer-Verlag, 1990).

Ruoslahti, E. et al., "Ary-Gly-Asp: A Versatile Cell Recognition Signal," *Cell*, 44, pp. 517-518 (Feb. 28, 1986).

Sampath, T. K. et al., "Bovine Osteogenic Protein is Composed of Dimers of OP-1 and BMP-2A, Two Members of the Transforming Growth Factor-$\beta$ Superfamily," *J. Biol. Chem.*, 265, pp. 13198-13205 (1990).

Seyedin, S. M. et al., "Purification and characterization of two cartilage-including factors from bovine demineralized bone," *Proc. Natl. Acad. Sci. USA*, 82, pp. 2267-2271 (Apr., 1985).

Seyedin, S. M. et al., "Cartilage-including Factor A, Apparent Identity to Transforming Growth Factor-$\beta$," *J. Biol. Chem.*, 261, pp. 5693-5695 (May 5, 1986).

Seyedin, S. M. et al., "Cartilage-inducing Factor-$\beta$ Is a Unique Protein Structurally and Functionally Related to Transforming Growth Factor-$\beta$," *J. Biol. Chem.*, 262, pp. 1946-1949 (Feb. 15, 1987).

Sporn, M. B. et al., "Some Recent Advances in the Chemistry and Biology of Transforming Growth Factor-$\beta$," *J. Cell Biol.*, 105, pp. 1039-1045 (Sep., 1987).

Urist, M. R. et al., "Purification of bovine morphogenetic protein by hydroxyapatite chromatography," *Proc. Natl. Acad. Sci.* (USA), 81, pp. 371-375 (1984).

Wahl, S. M. et al., "Transforming growth factor type $\beta$ induces monocyte chemotaxis and growth factor production," *Proc. Natl. Acad. Sci. USA*, 84, pp. 5788-5792 (Aug., 1987).

Wang, E. A. et al., "Purification and characterization of other distinct bone-inducing factors," *Proc. Natl. Natl. Acad. Sci.* (USA), 85, pp. 9484-9488 (1988).

Zapf, J. et al., "In vivo effects of the insulin-like growth factors (IGFs) in the hypophysectomized rat: comparison with human growth hormone and the possible role of the specific IGF carrier proteins," *Growth factors in biology and medicine*, pp. 169-186 (London: Pitman, 1985).

Zetter, B. R., "Migration of capillary endothelial cells is stimulated by tumour-derived factors," *Nature* (London), 285, pp. 41-43 (1980).

Kulyk, W. M., et al., "Promotion of embryonic chick limb cartilage differentiation by transforming growth factor-$\beta$" *Chemical Abstracts*, 111, p. 117 (209639v) (1989).

METHODS AND COMPOSITIONS FOR THE TREATMENT AND REPAIR OF DEFECTS OR LESIONS IN CARTILAGE OR BONE

TECHNICAL FIELD OF THE INVENTION

This invention relates to the treatment and repair of defects or lesions in cartilage or bone. More specifically, this invention relates to methods for treating defects or lesions (used interchangeably herein) in cartilage or bone and to compositions comprising a matrix containing one or more proliferating agents and a transforming factor to promote proliferation and transformation of cartilage repair cells to form new stable cartilage tissue and to compositions comprising a matrix containing an angiogenic factor to stimulate blood vessel formation and an osteogenic factor to stimulate formation of bone. The compositions and methods of this invention are particularly useful in the treatment of full-thickness defects found in severe osteoarthritis, and in other diseases and traumas that produce cartilage or bone injury.

BACKGROUND ART

Joints are one of the common ways bones in the skeleton are connected. The ends of normal articulated bones are covered by articular cartilage tissue, which permits practically frictionless movement of the bones with respect to one another [L. Weiss, ed., *Cell and Tissue Biology* (Munchen: Urban and Schwarzenburg, 1988) p. 247].

Articular cartilage is characterized by a particular structural organization. It consists of specialized cells (chondrocytes) embedded in an intercellular material (often referred to in the literature as the "cartilage matrix") which is rich in proteoglycans, collagen fibrils of predominantly type II, other proteins, and water [Buckwalter et al., "Articular Cartilage: Injury and Repair," in *Injury and Repair of the Musculoskeletal Soft Tissues* (Park Ridge, Ill.: American Academy of Orthopaedic Surgeons Symposium, 1987) p. 465]. Cartilage tissue is neither innervated nor penetrated by the vascular or lymphatic systems. However, in the mature joint of adults, the underlying subchondral bone tissue, which forms a narrow, continuous plate between the bone tissue and the cartilage, is innervated and vascularized. Beneath this bone plate, the bone tissue forms trabeculae, containing the marrow. In immature joints, articular cartilage is underlined by only primary bone trabeculae. A portion of the meniscal tissue in joints also consists of cartilage whose make-up is similar to articular cartilage [Beaupre, A. et al., *Clin. Orthop. Rel. Res.*, pp. 72-76 (1986)].

Two types of defects are recognized in articular surfaces, i.e., full-thickness defects and superficial defects. These defects differ not only in the extent of physical damage to the cartilage, but also in the nature of the repair response each type of lesion can elicit.

Full-thickness defects of an articular surface include damage to the hyaline cartilage, the calcified cartilage layer and the subchondral bone tissue with its blood vessels and bone marrow. Full-thickness defects can cause severe pain since the bone plate contains sensory nerve endings. Such defects generally arise from severe trauma or during the late stages of degenerative joint disease, such as osteoarthritis. Full-thickness defects may, on occasion, lead to bleeding and the induction of a repair reaction from the subchondral bone [Buckwalter et al., "Articular Cartilage: Composition, Structure, Response to Injury, and Methods of Facilitating Repair," in *Articular Cartilage and Knee Joint Function: Basic Science and Arthroscopy* (New York: Raven Press, 1990) pp. 19-56]. The repair tissue formed is a vascularized fibrous type of cartilage with insufficient biomechanical properties, and does not persist on a long-term basis [Buckwalter et al. (1990), supra].

Superficial defects in the articular cartilage tissue are restricted to the cartilage tissue itself. Such defects are notorious because they do not heal and show no propensity for repair reactions.

Superficial defects may appear as fissures, divots, or clefts in the surface of the cartilage, or they may have a "crab-meat" appearance in the affected tissue. They contain no bleeding vessels (blood spots) such as are seen in full-thickness defects. Superficial defects may have no known cause, but often they are the result of mechanical derangements which lead to a wearing down of the cartilaginous tissue. Mechanical derangements may be caused by trauma to the joint, e.g., a displacement of torn meniscus tissue into the joint, meniscectomy, a laxation of the joint by a torn ligament, malalignment of joints, or bone fracture, or by hereditary diseases. Superficial defects are also characteristic of early stages of degenerative joint diseases, such as osteoarthritis. Since the cartilage tissue is not innervated [*Ham's Histology* (9th ed.) (Philadelphia: J. B. Lippincott Co. 1987)., pp. 266-272] or vascularized, superficial defects are not painful. However, although painless, superficial defects do not heal and often degenerate into full-thickness defects.

It is generally believed that because articular cartilage lacks a vasculature, damaged cartilage tissue does not receive sufficient or proper stimuli to elicit a repair response [Webber et al., "Intrinsic Repair Capabilities of Rabbit Meniscal Fibrocartilage: A Cell Culture Model", (30th Ann. Orthop. Res. Soc., Atlanta, Feb. 1984); Webber et al., *J. Orthop. Res.*, 3, pp. 36-42 (1985)]. It is theorized that the chondrocytes in the cartilaginous tissue are normally not exposed to sufficient amounts of repair-stimulating agents such as growth factors and fibrin clots typically present in damaged vascularized tissue.

One approach that has been used to expose damaged cartilage tissue to repair stimuli involves drilling or scraping through the cartilage into the subchondral bone to cause bleeding [Buckwalter et al. (1990), supra]. Unfortunately, the repair response of the tissue to such surgical trauma is usually comparable to that observed to take place naturally in full-thickness defects that cause bleeding, viz., formation of a fibrous type of cartilage which exhibits insufficient biomechanical properties and which does not persist on a long-term basis [Buckwalter et al. (1990), supa].

A variety of growth factors have been isolated and are now available for research and biomedical applications [see e.g., Rizzino, A., *Dev. Biol.*, 130, pp. 411-422 (1988)]. Some of these growth factors, such as transforming growth factor beta (TGF-$\beta$), have been reported to promote formation of cartilage-specific molecules, such as type II collagen and cartilage-specific proteoglycans, in embryonic rat mesenchymal cells in vitro [e.g., Seyedin et al., *Proc. Natl. Acad. Sci. U.S.A.*, 82, pp. 226771 (1985); Seyedin et al., *J. Biol. Chem.*, 261. pp. 5693-95 (1986); Seyedin et al., *J. Biol. Chem.*, 262, pp. 1946-1949 (1987)].

Furthermore, a number of protein factors have been identified that apparently stimulate formation of bone. Such osteogenic factors include bone morphogenetic proteins, osteogenin, bone osteogenic protein (BOP), TGF-$\beta$s, and recombinant bone inducing proteins.

Millions of patients have been diagnosed as having osteoarthritis, i.e., as having degenerating defects or lesions in their articular cartilage. Nevertheless, despite claims of various methods to elicit a repair response in damaged cartilage, none of these treatments has received substantial application [Buckwalter et al. (1990), supra; Knutson et al., *J. Bone and Joint Surg.*, 68-B, p. 795 (1986); Knutson et al., *J. Bone and Joint Surg.*, 67-B, p. 47 (1985); Knutson et al., *Clin. Orthop.*, 191, p. 202 (1984); Marquet, *Clin. Orthop.*, 146, p. 102 (1980)]. And such treatments have generally provided only temporary relief. Systemic use of "chondroprotective agents" has also been purported to arrest the progression of osteoarthritis and to induce relief of pain. However, such agents have not been shown to promote repair of lesions or defects in cartilage tissue.

To date, treatment of patients suffering from osteoarthritis has been directed largely to symptomatic relief through the use of analgesics and anti-inflammatory agents. Without a treatment that will elicit repair of superficial defects in articular cartilage, the cartilage frequently wears down to the subchondral bone plate. At this phase of the disease, i.e., severe osteoarthritis, the unremitting nature of the pain and the significant compromise of function often dictates that the entire joint be excised and replaced with an artificial joint of metal and/or plastic. Some one-half million procedures comprising joint resection and replacement with an artificial joint are currently performed on knees and hips each year. [See e.g., Graves, E. J., "1988 Summary; National Hospital Discharge Survey", *Advanced Data From Vital and Health Statistics*, 185, pp. 1-12 (June 19, 1990)].

There is, therefore, a need for a reliable treatment for cartilage in superficial cartilage defects, e.g., as found in the early stages of osteoarthritis. There is also a need for treatment of cartilage or bone defects as found in the lesions of severe osteoarthritis and for the treatment of other bone defects.

SUMMARY OF THE INVENTION

The present invention solves the problems referred to above by providing effective therapeutic methods and compositions to induce the repair of lesions in cartilage or bone of humans and other animals. Use of the methods and compositions of this invention also promote the healing of traumatic lesions and forms of osteoarthritis which would otherwise lead to loss of effective joint function leading to probable resection and replacement of the joint.

In general outline, the methods of this invention for repairing full-thickness defects in joints comprise filling the defect in the bone portion of a full-thickness defect up to the level of the bone-cartilage interface with a matrix that will be incorporated into the animal tissue and is generally biodegradable. The matrix contains angiogenic and osteogenic factors. This matrix filling the bone defect is then covered with a membrane, which is impermeable to cells. The membrane is sealed to the edges of the defect at the cartilage-bone junction, e.g., by sealing to the cartilage by thermal bonding using a thermal knife or laser. The remaining cartilage portion of the defect is filled to the top of the cartilage surface with a matrix which contains a chondrogenic composition, and which will be incorporated into the animal tissue and is generally biodegradable. The matrix containing angiogenic and osteogenic factors may also be applied to any bone defect to promote repair. The methods of this invention for repairing bone defects that do not involve cartilage, combine filling the bone defect with a matrix containing angiogenic factor(s) and osteogenic factor(s). The osteogenic factor(s) is packaged in an appropriate delivery system.

Treatment of full-thickness defects can be effected during arthroscopic, open surgical or percutaneous procedures using the methods of this invention. According to certain methods of this invention, after identification of the defect, the defect is treated by the steps of (1) filling the bone portion of the defect with a composition comprising a matrix containing an angiogenic factor and an osteogenic factor packaged in an appropriate delivery system, e.g., liposomes; (2) placing a membrane, preferably a biodegradable membrane, which prevents cells from migrating from the bone defect side to the cartilage defect side, over the matrix in the bone defect and sealing the membrane to the edges of the defect at the cartilage-bone junction; and (3) filling the cartilage portion of the defect with a composition comprising a matrix, preferably biodegradable, and containing a proliferation agent and a transforming factor which is packaged in an appropriate delivery system. In this last step, the matrix is bonded to the surface of the cartilage portion of the full-thickness defect, for example, by using an adhesion-promoting factor, such as transglutaminase.

DETAILED DESCRIPTION OF INVENTION

In order that the invention may be more fully understood, the following detailed description is provided. In the description the following terms are used.

Angiogenic Factor—as used herein, refers to any peptide, polypeptide, protein or any other compound or composition which induces or stimulates the formation of blood vessels and associated cells (such as endothelial, perivascular, mesenchymal and smooth muscle cells) and blood vessel-associated basement membranes. In vivo and in vitro assays for angiogenic factors are well-known in the art [e.g., Gimbrone, M. A., et al., *J. Natl. Cancer Inst.*, 52, pp. 413-419 (1974); Klagsbrun, M. et al., *Cancer Res.*. 36, pp. 110-113 (1976); Gross et al., *Proc. Natl. Acad. Sci. (U.S.A.)*, 80, pp. 2623-2627 (1983); Gospodarowicz et al., *Proc. Natl. Acad. Sci. (U.S.A.)*, 73, pp. 4120-4124 (1976); Folkman et al., *Proc. Natl. Acad. Sci. (U.S.A.)*, 76, pp. 5217-5221 (1979); Zetter, B. R., *Nature (London)*, 285, pp. 41-43 (1980); Azizkhan, R. G. et al., *J. Exp. Med.*, 152, pp. 931-944 (1980)].

Arthroscopy—as used herein, refers to the use of an arthroscope to examine or perform surgery on a joint.

Bone—as used herein, refers to a calcified connective tissue primarily comprising a network of deposited calcium and phosphate in the form of hydroxyapatite, collagen (predominantly type I collagen) and bone cells, such as osteoblasts and osteoclasts.

Bone Repair Cell—as used herein, refers to a cell which, when exposed to appropriate stimuli, will differentiate and be transformed into a bone cell, such as an osteoblast or an osteocyte, which forms bone. Bone repair cells include perivascular cells, mesenchymal cells, fibroblasts, fibroblast-like cells and dedifferentiated chondrocytes.

Cartilage—as used herein, refers to a type of connective tissue that contains chondrocytes embedded in an intercellular material (often referred to as the "cartilage matrix") comprising fibrils of collagen (predominantly type II collagen along with other minor types, e.g., types IX and XI), various proteoglycans (e.g., chondroitinsulfate-, keratansulfate-, and dermatansulfate proteoglycans), other proteins, and water. Cartilage as used herein includes articular and meniscal cartilage. Articular cartilage covers the surfaces of the portions of bones in joints and allows movement in joints without direct bone-to-bone contact, and thereby prevents wearing down and damage to apposing bone surfaces. Most normal healthy articular cartilage is also described as "hyaline", i.e., having a characteristic frosted glass appearance. Meniscal cartilage is usually found in joints which are exposed to concussion as well as movement. Such locations of meniscal cartilage include the temporo-mandibular, sterno-clavicular, acromioclavicular, wrist and knee joints [*Gray's Anatomy* (New York: Bounty Books, 1977)].

Cartilage Repair Cell—as used herein, refers to a cell which, when exposed to appropriate stimuli, will differentiate and be transformed into a chondrocyte. Cartilage repair cells include mesenchymal cells, fibroblasts, fibroblast-like cells, macrophages and dedifferentiated chondrocytes.

Cell Adhesion Promoting Factor—as used herein, refers to any compound or composition, including fibronectin and other peptides as small as tetrapeptides which comprise the tripeptide Arg-Gly-Asp, which mediates the adhesion of cells to extracellular material [Ruoslathi et al., *Cell.* 44, pp. 517-518 (1986)].

Chemotactic Agent—as used herein, refers to any compound or composition, including peptides, proteins, glycoproteins and glycosaminoglycan chains, which is capable of attracting cells in standard in vitro chemotactic assays [e.g., Wahl et al., *Proc. Natl. Acad. Sci. U.S.A.*, 84, pp. 5788-92 (1987); Postlewaite et al., *J. Exp. Med.*, 165, pp. 251-56 (1987); Moore et al., *Int. J. Tiss. Reac.*, XI, pp. 301-07 (1989)].

Chondrocytes—as used herein, refers to cells which are capable of producing components of cartilage tissue, e.g., type II cartilaginous fibrils and fibers and proteoglycans.

Fibroblast growth factor (FGF)—any member of the family of FGF polypeptides [Gimenez-Gallego et al., *Biochem. Biophys. Res. Commun.*, 135, pp. 541-548 (1986); Thomas et al., *Trends Biochem. Sci.*, 11, pp. 81-84 (1986)] or derivatives thereof, obtained from natural, synthetic or recombinant sources, which exhibits the ability to stimulate DNA synthesis and cell division in vitro [for assays see, e.g., Gimenez-Gallego et al., 1986, supra; Canalis et al., *J. Clin. Invest.*, 81, pp. 1572-1577 (1988)] of a variety of cells, including primary fibroblasts, chondrocytes, vascular and corneal endothelial cells, osteoblasts, myoblasts, smooth muscle and glial cells [Thomas et al., 1986, supra]. FGFs may be classified as acidic (aFGF) or basic (bFGF) FGF, depending on their isoelectric points (pI).

Matrix—as used herein, refers to a porous composite, solid or semi-solid substance having pores or spaces sufficiently large to allow cells to populate the matrix. The term matrix includes matrix-forming materials, i.e., materials which can form matrices within a defect site in cartilage or bone. Matrix-forming materials may require addition of a polymerizing agent to form a matrix, such as adding thrombin to a solution containing fibrinogen to form a fibrin matrix. Other matrix materials include collagen, combinations of collagen and fibrin, agarose (e.g., Sepharose ®), and gelatin. Calcium phosphate may be used alone or in combination with other matrix materials in treating defects in bones.

Membrane—as used herein, refers to any material which can be placed between the bone defect portion and the cartilage defect portion of a full thickness defect and which prevents cell migration and blood vessel infiltration from the bone defect portion into the cartilage defect portion of the full thickness defect. The membranes used in the methods and compositions of this invention for the repair of full thickness defects are preferably biodegradable.

Osteogenic Factor—as used herein, refers to any peptide, polypeptide, protein or any other compound or composition which induces or stimulates the formation of bone. The osteogenic factor induces differentiation of bone repair cells into bone cells, such as osteoblasts or osteocytes. This process may be reached via an intermediary state of cartilage tissue. The bone tissue formed from bone cells will contain bone specific substances such as type I collagen fibrils, hydroxyapatite mineral and various glycoproteins and small amounts of bone proteoglycans.

Proliferation (mitogenic) Agent—as used herein, refers to any compound or composition, including peptides, proteins, and glycoproteins, which is capable of stimulating proliferation of cells in vitro. In vitro assays to determine the proliferation (mitogenic) activity of peptides, polypeptides and other compounds are well-known in the art [see, e.g., Canalis et al., *J. Clin. Invest.*, pp. 1572-77 (1988); Gimenez-Gallego et al., *Biochem. Biophys. Res. Commun.*, 135, pp. 541-548 (1986); Rizzino, "Soft Agar Growth Assays for Transforming Growth Factors and Mitogenic Peptides", in *Methods Enzymol.*, 146A (New York: Academic Press, 1987), pp. 341-52; Dickson et al., "Assay of Mitogen-Induced Effects on Cellular Incorporation of Precursors for Scavengers, de Novo, and Net DNA Synthesis", in *Methods Enzymol.*, 146A (New York: Academic Press, 1987), pp. 329-40]. One standard method to determine the proliferation (mitogenic) activity of a compound or composition is to assay it in vitro for its ability to induce anchorage-independent growth of nontransformed cells in soft agar [e.g., Rizzino, 1987, supra]. Other mitogenic activity assay systems are also known [e.g., Gimenez-Gallego et al., 1986, supra; Canalis et al., 1988, supra; Dickson et al., 1987, supra]. Mitogenic effects of agents are frequently very concentration-dependent, and their effects can be reversed at lower or higher concentrations than the optimal concentration range for mitogenic effectiveness.

Transforming Factor—as used herein, refers to any peptide, polypeptide, protein, or any other compound or composition which induces differentiation of a cartilage repair cell into a chondrocyte. The ability of the compound or composition to induce or stimulate production of cartilage-specific proteoglycans and type II collagen by cells can be determined by in vitro assays known in the art [Seyedin et al., *Proc. Natl. Acad. Sci. U.S.A.*, 82, pp. 2267-71 (1985); Seyedin et al., *Path. Immunol. Res.*, 7, pp. 38-42 (1987)].

Transforming Growth Factor Beta (TGF-$\beta$)—any member of the family of TGF-$\beta$ polypeptides [Derynck, R. et al., *Nature*, 316, pp. 701-705 (1985); Roberts et al., "The transforming growth factor-$\beta$'s", In *Peptide growth factors and their receptors I* (Berlin:

Springer Verlag, 1990), p. 419)] or derivatives thereof, obtained from natural, synthetic or recombinant sources, which exhibits the characteristic TGF-$\beta$ ability to stimulate normal rat kidney (NRK) cells to grow and form colonies in a soft agar assay [Roberts et al., "Purification of Type $\beta$ Transforming Growth Factors From Nonneoplastic Tissues", in *Methods for Preparation of Media, Supplements, and Substrata for Serum-Free Animal Cell Culture* (New York: Alan R. Liss, Inc., 1984)] and which is capable of inducing transformation of cartilage repair cells into chondrocytes as evidenced by the ability to induce or stimulate production of cartilage-specific proteoglycans and type II collagen by cells in vitro [Seyedin et al., 1985, supra].

This invention relates to compositions and methods for treating defects or lesions in cartilage or bone. The compositions of this invention comprise matrices having pores sufficiently large to allow cells to populate the matrices.

For use in the repair of cartilage as in superficial defects or the cartilage layer in a full-thickness defect, the matrix will also contain a proliferation agent to stimulate the proliferation of cartilage repair cells in the matrix. Preferably, the proliferation agent also serves as a chemotactic agent to attract cartilage repair cells to the matrix. Alternatively, the matrix may contain a chemotactic agent in addition to the proliferation agent. In one preferred embodiment of this invention, the matrix also contains an appropriate concentration of a transforming factor, the transforming factor being contained within or in association with a delivery system which effects release of the transforming factor at the appropriate time to transform the proliferated cartilage repair cells in the matrix into chondrocytes which produce stable cartilage tissue. The matrix may also contain a cell adhesion promoting factor.

Matrix materials useful in the methods and compositions of this invention for filling or otherwise dressing the cartilage or bone defects include fibrinogen (activated with thrombin to form fibrin in the defect or lesion), collagen, agarose, gelatin and any other biodegradable material which forms a matrix with pores sufficiently large to allow cartilage or bone repair cells to populate and proliferate within the matrix and which can be degraded and replaced with cartilage or bone during the repair process. In some instances, calcium phosphate containing compounds may be used alone or in combination with other biodegradable matrix materials in treating bone defects.

The matrices useful in the compositions and methods of this invention may be preformed or may be formed in situ, for example, by polymerizing compounds and compositions such as fibrinogen to form a fibrin matrix. Matrices that may be preformed include collagen (e.g., collagen sponges and collagen fleece), chemically modified collagen, gelatin beads or sponges, a gel-forming substance such as agarose, and any other gel-forming or composite substance that is composed of a matrix material that will fill the defect and allow cartilage or bone repair cells to populate the matrix, or mixtures of the above.

In one embodiment of this invention, the matrix is formed using a solution of fibrinogen, to which is added thrombin to initiate polymerization shortly before use. A fibrinogen concentration of 0.5–5 mg/ml of an aqueous buffer solution may be used. Preferably, a fibrinogen solution of 1 mg/ml of an aqueous buffer solution is used. Polymerization of this fibrinogen solution in the defect area yields a matrix with a pore size sufficiently large (e.g., approximately 50–200 $\mu$m) so that cartilage or bone repair cells are free to populate the matrix and proliferate in order to fill the volume of the defect that the matrix occupies. Preferably, a sufficient amount of thrombin is added to the fibrinogen solution shortly before application in order to allow enough time for the surgeon to deposit the material in the defect area prior to completion of polymerization. Typically, the thrombin concentration should be such that polymerization is achieved within a few to several (2–4) minutes since exposure of cartilage to air for lengthy periods of time has been shown to cause damage [Mitchell et al., *J. Bone Joint Surg.*, 71A, pp. 89–95 (1989)]. Excessive amounts of thrombin should not be used since thrombin has the ability to cleave growth factor molecules and inactivate them. Thrombin solutions of 10–500 units per ml, and preferably 100 units per ml, of an aqueous buffer solution may be prepared for addition to the fibrinogen solution. In a preferred embodiment of this invention, approximately 20 $\mu$l of thrombin (100 U/ml) are mixed with each ml of a fibrinogen solution (1 mg/ml) approximately 200 seconds before filling the defect. Polymerization will occur more slowly if a lower concentration of thrombin is added. It will be appreciated that the amount of thrombin solution needed to achieve fibrin polymerization within 2–4 minutes can be given only approximately, since it depends upon the environmental temperature, the temperature of the thrombin solution, the temperature of the fibrinogen solution, etc. The polymerization of the thrombin-activated matrix solution filling the defect is easily monitored by observing the thrombin-induced polymerization of an external sample of the fibrinogen solution. Preferably, in the compositions and methods of this invention, fibrin matrices are formed from autologous fibrinogen molecules, i.e., fibrinogen molecules derived from the blood of the same mammalian species as the species to be treated. Non-immunogenic fibrinogen from other species may also be used.

Matrices comprising fibrin and collagen may also be used in the compositions and methods of this invention. In a preferred embodiment of this invention, collagenous matrices are used in repairing bone defects.

When collagen is used as a matrix material, sufficiently viscous solutions can be made, e.g., using Collagen-Vliess ® ("fleece"), Spongostan ®, or gelatine-blood-mixtures, and there is no need for a polymerizing agent. Collagen matrices may also be used with a fibrinogen solution activated with a polymerizing agent so that a combined matrix results.

Polymerizing agents may also be unnecessary when other biodegradable compounds are used to form the matrix. For example, Sepharose ® solutions may be chosen that will be liquid matrix solutions at 39°–42° C. and become solid (i.e., gel-like) at 35°–38° C. The Sepharose should also be at concentrations such that the gel filling the defect has a mesh size to allow bone or cartilage repair cells to freely populate the matrix and defect area.

In the compositions of this invention used in cartilage repair, one or more proliferation (mitogenic) agents may be added to the matrix solution. The proliferation agent or agents should be present in an appropriate concentration range to have a proliferative effect on cartilage repair cells in the matrix filling the defect. Preferably, the same agent should also have a chemotactic effect on the cells (as in the case of TGF-$\beta$);

however, a factor having exclusively a proliferative effect may be used. Alternatively, to produce chemotactic cell immigration, followed by induction of cell proliferation, two different agents may be used, each one having just one of those specific effects (either chemotactic or proliferative).

Proliferation (mitogenic) agents useful in the compositions and methods of this invention for stimulating the proliferation of cartilage repair cells include transforming growth factors ("TGFs") such as TGF-αs and TGF-βs; insulin-like growth factor ("IGF I"); acidic or basic fibroblast growth factors ("FGFs"); platelet-derived growth factor ("PDGF"); epidermal growth factor ("EGF"); and hemopoietic growth factors, such as interleukin 3 ("IL-3") [Rizzino, 1987, supra; Canalis et al., supra, 1988; *Growth factors in biology and medicine, Ciba Foundation Symposium*, 116 (New York: John Wiley & Sons, 1985); Baserga, R., ed., *Cell growth and division* (Oxford: IRL Press, 1985); Sporn, M. A. and Roberts, A. B., eds., *Peptide growth factors and their receptors*, Vols. I and II (Berlin: Springer-Verlag, 1990)]. However, these particular examples are not limiting. Any compound or composition which is capable of stimulating the proliferation of cells as demonstrated by an in vitro assay for cell proliferation is useful as a proliferation agent in this invention. Such assays are known in the art [e.g., Canalis et al., 1988, supra; Gimenez-Gallego et al., 1986, supra; Dickson et al., 1987, supra; Rizzino, 1987, supra].

Chemotactic agents useful in the compositions and methods of this invention for attracting cartilage repair cells to the cartilage defect include, for example, TGF-βs, FGFs (acid or basic), PDGF, tumor necrosis factors (e.g., TNF-α, TNF-β) and proteoglycan degradation products, such as glycosaminoglycan chains [Roberts et al. (1990), supra; *Growth factors in biology and medicine, Ciba Foundation Symposium*, 116 (New York, John Wiley & Sons, 1985); R. Baserga, ed., *Cell growth and division* (Oxford: IRL Press, 1985)]. Assays to determine the chemotactic ability of polypeptides and other compounds are known in the art [e.g., Postlewaite et al., 1987, supra; Wahl et al., 1987, supra; Moore et al., 1989, supra].

In a preferred embodiment of this invention, the matrix used in cartilage repair contains TGF-β as the proliferation agent and as the chemotactic agent. In particular, TGF-βI or TGF-βII may be used as the proliferation and chemotactic agent. Other TGF-β forms (e.g., TGF-βIII, TGF-βIV, TGF-βV, etc.) or polypeptides having TGF-β activity [see Roberts, 1990, supra] may also be useful for this purpose, as well as other forms of this substance to be detected in the future, and other growth factors. For use as the proliferation agent and chemotactic agent, TGF-β molecules are dissolved or suspended in the matrix at a concentration of preferably 2–50 ng/ml of matrix solution, and most preferably, 2–10 ng/ml of matrix solution. It will be appreciated that the preferred concentration of TGF-β that will stimulate proliferation of cartilage repair cells may vary with the particular animal to be treated.

A transforming factor or factors may also be present in the matrix solution used in cartilage repair so that after cartilage repair cells have populated the matrix, the transforming factor will be released into the defect site in a concentration sufficient to promote differentiation (i.e., transformation) of the cartilage repair cells into chondrocytes which form new stable cartilage tissue. Proper timing of the release of the transforming factor is particularly important if the transforming factor can inhibit or interfere with the effectiveness of the proliferation agent [see Roberts et al. (1990), supra].

Transforming factors useful in the compositions and methods of this invention to promote cartilage repair include any peptide, polypeptide, protein or any other compound or composition which induces differentiation of cartilage repair cells into chondrocytes which produce cartilage-specific proteoglycans and type II collagen. The ability of a compound or composition to induce or stimulate production of cartilage-specific proteoglycans and type II collagen in cells can be determined using assays known in the art [e.g., Seyedin et al., 1985, supra; Seyedin et al., 1987, supra]. The transforming factors useful in the compositions and methods of this invention include, for example, TGF-βs, TGF-αs and FGFs (acid or basic). These transforming factors may be used singly or in combination. In addition, TGF-β may be used in combination with EGF.

The properly timed release of the transforming factor may be achieved by packaging the transforming factor in or with an appropriate delivery system. Delivery systems useful in the compositions and methods of this invention include liposomes, bioerodible polymers, carbohydrate-based corpuscles, water-oil emulsions, fibers such as collagen which are chemically linked to heparin sulfate proteoglycans or other such molecules to which transforming factors bind spontaneously, and osmotic pumps. Delivery systems such as liposomes, bioerodible polymers, fibers with bound transforming factors and carbohydrate-based corpuscles containing the transforming agent may be mixed with the matrix solution used to fill the defect. These systems are known and available in the art [see P. Johnson and J. G. Lloyd-Jones, eds., *Drug Delivery Systems* (Chichester, England: Ellis Horwood Ltd., 1987)]. Liposomes may be prepared according to the procedure of Kim et al., *Biochem. Biophys. Acta*, 728, pp. 339–348 (1983). Other liposome preparation procedures may also be used. Additional factors for stimulating chondrocytes to synthesize the cartilage tissue components may be included with the transforming factor in the delivery system.

In a preferred embodiment of this invention, the matrix used in cartilage repair contains TGF-β as the proliferation and chemotactic agent, and contains TGF-β packaged in a delivery system as the transforming factor. In particular, TGF-βI or TGF-βII may be used as the proliferation and chemotactic agent and as the transforming factor. Other TGF-β forms (e.g., TGF-βIII, TGF-βIV, TGF-βV, etc.) or polypeptides having TGF-β activity (see Roberts, 1990, supra) may also be useful for this purpose, as well as other forms of this substance to be detected in the future, and other growth factors.

In a preferred embodiment for cartilage repair, a TGF-β concentration of preferably 2–50 ng/ml of matrix solution, and most preferably, 2–10 ng/ml of matrix solution, is used as a proliferation agent and as a chemotactic agent. A substantially higher concentration of TGF-β is also present in a subsequently releasable form in the matrix composition as a transforming factor. Preferably, the subsequent concentration of TGF-β is greater than 200 ng/ml of matrix and, most preferably, is greater than 500 ng/ml of matrix. It will be appreciated that the preferred concentration of TGF-β to induce differentiation of cartilage repair cells may vary with the particular animal to be treated.

It is necessary to stagger the exposure of the cartilage repair cells to the two concentration ranges of TGF-$\beta$, since TGF-$\beta$ at relatively high concentrations (e.g., greater than 200 ng/ml of matrix solution) may not only transform cartilage repair cells into chondrocytes, but also will inhibit chemotactic attraction of cartilage repair cells; whereas at relatively low concentrations (e.g., 2-10 ng/ml), TGF-$\beta$ attracts cartilage repair cells and stimulates their proliferation, but will not induce transformation of cartilage repair cells into chondrocytes which produce cartilage tissue.

In a preferred embodiment of this invention, in order to obtain the sequence of chemotaxis and proliferation, followed by transformation, TGF-$\beta$ is present both in a free, unencapsulated form and in an encapsulated, or otherwise sequestered, form in the matrix. Preferably, for the purpose of attracting and inducing proliferation of cartilage repair cells in the matrix and defect area, TGF-$\beta$ molecules are dissolved or suspended in the matrix at a concentration of 2-10 ng/ml of matrix solution. To promote transformation of cartilage repair cells in the matrix into chondrocytes, TGF-$\beta$ molecules are also present in the matrix sequestered in multivesicular liposomes according to the method of Kim et al., 1983, supra, at a concentration of greater than 200 ng/ml of matrix solution, and preferably at a concentration of greater than 500 ng/ml. The TGF-$\beta$-loaded liposomes are disrupted when the attracted cartilage repair cells have populated the matrix and have started to degrade the matrix. During the degradation of the matrix, the cartilage repair cells ingest and/or degrade the liposomes, resulting in the release of TGF-$\beta$ at concentrations sufficient to induce the transformation of cartilage repair cells into chondrocytes.

The required two-stage delivery of chemotactic and proliferating versus transforming concentrations of TGF-$\beta$ may also be achieved by combining transforming concentrations of TGF-$\beta$ with a bioerodible polymer. Alternatively, a pump, and preferably an implanted osmotic pump, may be used to control the concentration of TGF-$\beta$ in the defect and matrix. In this embodiment of the invention, the pump controls the concentration of TGF-$\beta$ in the matrix, i.e., the pump may release TGF-$\beta$ at an initial chemotactic and proliferation stimulating concentration and at a subsequent transforming concentration. Preferably, the transforming concentration of TGF-$\beta$ is delivered by the pump approximately 1 to 2 weeks post-operatively. Delivery of the transforming factor into the defect volume is preferably localized to the matrix in the defect site.

The proliferation agents and, when used, the transforming factors in the compositions of this invention are applied in the defect site within the matrix. Their presence is thus restricted to a very localized site. This is done to avoid their free injection or infusion into a joint space. Such free infusion may produce the adverse effect of stimulating the cells of the synovial membrane to produce joint effusion.

In the compositions of this invention used in bone repair, one or more angiogenic factors is added to the matrix solution to stimulate the formation and ingrowth of blood vessels and associated cells (e.g., endothelial, perivascular, mesenchymal and smooth muscle cells) and of basement membranes in the area of the bone defect. Angiogenic factors useful in the compositions and methods of this invention for stimulating vascularization throughout the deposited matrix in the area of the bone defect include bFGF, TGF-$\beta$, PDGF, TNF-$\alpha$, angiogenin or angiotropin. Heparin sulfate has been found to enhance the angiogenic activity of bFGF. In a preferred embodiment of this invention, bFGF and heparin sulfate are dissolved, suspended or bound in a matrix at a concentration of approximately 10 ng/ml of matrix solution. The preferred concentrations for other angiogenic factors are: 5 ng/ml of matrix solution for TGF-$\beta$, 10 ng/ml of matrix solution for TNF-$\alpha$, and 10 ng/ml of matrix solution for PDGF. However, bFGF in combination with heparin sulfate is the most preferred angiogenic factor among the above named angiogenic factors.

An osteogenic factor is also present in the matrix solution used in bone repair so that after blood vessels and associated cells have populated the matrix, the osteogenic factor is released into the bone defect site as the matrix is degraded in a concentration sufficient to promote a process leading to the eventual development of osteoblasts and osteocytes. The osteogenic factor is sequestered or packaged in an appropriate delivery system within the matrix and is released as the matrix is degraded. The delivery systems used in the cartilage repair compositions are useful in the bone repair compositions of this invention, e.g., liposomes or carbohydrate-based corpuscles (see supra). In one embodiment of this invention, the matrix used in bone repair contains TGF-$\beta$ packaged in a delivery system as the osteogenic factor, at a concentration of 100 ng/ml of matrix solution. Lower and higher concentrations of TGF-$\beta$ may be used.

Osteogenic factors useful in the bone repair compositions of this invention include any peptide, polypeptide, protein or any other compound or composition which induces differentiation of bone repair cells into bone cells, such as osteoblasts and osteocytes, which produce bone tissue. The osteogenic factors useful in this invention include proteins such as TGF-$\beta$ [Sampath, T. R. et al., *J. Biol. Chem.*, 65(22), pp. 13198-13205 (1990)], osteogenin [Luyten, F. P. et al., *J. Biol. Chem.*, 264(15). pp. 13377-80 (1989)], bone morphogenic protein (BMP) [Wang, E. et al., *Proc. Natl. Acad. Sci. U.S.A.*, 87, pp. 2220-24 (1990)], and TGF-$\beta$ combined with epidermal growth factor (EGF).

The differentiation of mesenchymal cells induced by an osteogenic factor may include the formation of intermediary tissues such as fibrous, hyaline and calcified cartilage; and endochondral ossification, which leads to the formation of woven bone tissue, which will become remodelled and transformed into mature lamellar bone tissue. In some instances, bone may be formed directly from mesenchymal cells without the appearance of an intermediary tissue. Within the matrix, the process of bone tissue formation usually occurs 3 to 4 weeks after blood vessels have formed and infiltrated the matrix in response to the angiogenic factor present in the matrix.

The matrix compositions described in this invention for repairing the bone portion of a fullthickness defect in joints are also useful in treating any defect in bone tissue as is desirable. Such defects include bone fractures, joint fractures, non-unions and delayed unions, percutaneous arthrodesis, pseudo-arthrosis and bone defects resulting from congenital defects, trauma, tumor infection, degenerative disease and other causes of loss of skeletal tissue. The bone repairing matrix compositions are also useful for prosthesis implantation and enhancement of prosthesis stability, enhancement of osseointegration of implant materials used for internal fixation procedures, stabilization of dental implant materials, healing acceleration of ligament insertion, and spine or other joint fusion procedures.

Fibronectin or any other compound, including peptides as small as tetrapeptides, that contain the amino acid sequence Arg-Gly-Asp, may be used as cell adhesion promoting factors [Ruoslathi et al., *Cell*, 44, pp. 517-18 (1986)] in order to enhance the initial adhesion of cartilage or bone repair cells to a matrix deposited in a defect site. Fibrin and certain collagen matrices already contain this sequence [Ruoslathi et al., 1986, supra]. When other biodegradable matrices are used, such cell adhesion promoting factors may be mixed with the matrix material before the matrix is used to fill or dress the defect. Peptides containing Arg-Gly-Asp may also be chemically coupled to the matrix material (e.g., to its fibers or meshes) or to a compound added to the matrix, such as albumin.

The compositions hereinbefore described are useful in methods to induce cartilage or bone formation at a selected site of defect in cartilage or bone tissue of an animal.

The methods of this invention allow for a treatment of cartilage and bone defects in animals, including humans, that is simple to administer and is restricted in location to an affected joint area. The entire treatment may be carried out by arthroscopic, open surgical or percutaneous procedures.

To carry out the methods of treating defects or lesions in cartilage or bone according to this invention, a defect or lesion is identified, prepared, and filled with the matrix compositions according to this invention.

In the case of repairing a defect in bone tissue, an angiogenic factor is present in the bone repair composition at an appropriate concentration to stimulate formation of blood vessels within the matrix filling the bone defect. As blood vessels are formed, the osteogenic factor is released from its delivery system to induce the process of bone formation.

For cartilage repair, a proliferation (mitogenic) agent is present in the matrix composition at an appropriate concentration to stimulate the proliferation of cartilage repair cells in the matrix and defect or lesion. The same agent may also, at this concentration, serve as a chemotactic agent to attract cartilage repair cells, provided that the factor used has a combined effect with respect to cell proliferation and chemotaxis (as does TGF-β at 2-10 ng/ml of matrix). Alternatively, two different agents may be present in the matrix, one with a specific proliferative effect, and the other with a specific chemotactic effect. In an alternative embodiment, after the defect area is dressed with the matrix, the proliferation agent and, if desired, a chemotactic agent, may be injected directly into the matrix-filled defect area.

In a subsequent step of cartilage repair, the cartilage repair cells in the matrix are exposed to a transforming factor at the appropriate time at a concentration sufficient to transform the cartilage repair cells into chondrocytes which produce stable cartilage tissue. This may be accomplished by including an appropriate delivery system containing the transforming factor within the matrix composition as described above. Alternatively, the transforming agent may be delivered by injection directly into the matrix-filled defect area at the appropriate time. The transforming concentration should be made available to the cells approximately 1 to 2 weeks following the initial implantation of the matrix into the defect area. Additional factors may be added to the delivery system or directly injected in order to better promote synthesis of the cartilage matrix components at this time point.

Cartilage or bone defects in animals are readily identifiable visually during arthroscopic examination of the joint or during simple examination of the lesion or defect during open surgery. Cartilage or bone defects may also be identified inferentially by using computer aided tomography (CAT scanning) X-ray examination, magnetic resonance imaging (MRI) analysis of synovial fluid or serum markers, or by any other procedure known in the art.

According to the methods of this invention, the bone defect site of a full-thickness defect is filled up to the calcified cartilage layer at the bone-cartilage interface with a bone repair matrix composition such that a flat plane is formed. Thereafter, a membrane, preferably a biodegradable membrane, which is impermeable to cells (e.g., pore sizes less than 5 μm), is placed over the matrix-filled bone defect, and the edges of the membrane sealed to the perimeter of the defect in the region of the cartilage-bone junction. Preferably, the membrane is sealed to the cartilage at the junction by thermal bonding using a thermal knife or laser. The matrix composition comprises a matrix material, an angiogenic factor, and an osteogenic factor, which is packaged in an appropriate delivery system.

The purpose of the membrane is to prevent blood vessels from infiltrating the layer of cartilage in the case of a full-thickness defect. The formation of blood vessels in the cartilage stimulates bone formation in the cartilage and inhibits complete repair of the cartilage layer. If only a bone defect needs to be repaired, no membrane has to be applied.

After the membrane has been placed over the matrix-filled bone defect and sealed to the perimeter of the defect in the region of the cartilage-bone junction, the remaining portion of the defect is completely filled with a matrix composition used to stimulate cartilage repair. The composition for cartilage repair comprises a matrix material and a proliferation agent and, if desired, a chemotactic agent. The composition used in this step may also contain, packaged in an appropriate delivery system, a transforming factor. In the most preferred method of cartilage repair of the invention, the matrix contains a proliferation agent, a chemotactic agent (which may be identical to the proliferation agent) and a transforming factor which is packaged in or associated with a delivery system that releases the transforming factor, at a time that the repair cells populating the matrix have begun remodelling the intercellular substance, at a concentration that transforms the cartilage repair cells into chondrocytes. Preferred compositions are described above.

The adhesion of a matrix to cartilage in a superficial defect or to the cartilage portion of a full-thickness defect can be enhanced by treating the cartilage defect with transglutaminase [see, e.g., Ichinose et al., *J. Biol. Chem.*, 265 (3), pp. 13411-14 (1990); Najjar, V. A. and Lorand, L., eds. *Transglutaminases* (Boston: Martinus-Nijhoff, 1984). In this embodiment of the invention, the cartilage defect is dried, e.g. by using cottonoid, and filled with a solution of transglutaminase. The solution is then removed, e.g., by suction, leaving a film containing transglutaminase on the cartilage. The defect is then filled with a matrix composition described above for cartilage repair.

Additional details and examples describing methods and compositions for the treatment and repair of defects in cartilage are described in a commonly owned U.S. patent application Ser. No. 648,274, now U.S. Pat. No. 5,206,023, and are incorporated herein by reference.

In order that the invention described herein may be more fully understood, the following examples are set forth. It should be understood that these examples are for illustrative purposes and are not to be construed as limiting this invention in any manner.

EXAMPLE

Repair Of Full-Thickness Defects In Articular Cartilage

Full-thickness articular cartilage defects, 0.7 mm in width, were created in the medial condyles and patellar grooves of adult mini-pig knee joints. Lesions were effected in a group of four animals maintained under general anaesthesia, using a planing instrument. The vertical extensions of each lesion into the subchondral bone (containing blood vessels and bone marrow cells) was controlled macroscopically by the occurrence of bleeding to insure that a full-thickness lesion had been made in the joint. The depth of the defect was filled in with a collagenous matrix, containing free TGF-$\beta$ at a concentration of about 4 ng/ml of matrix solution, and liposome-encapsulated TGF-$\beta$ at a concentration of about 100 ng/ml of matrix volume. This osteogenic matrix composition was applied up to the cartilage-bone junction, at which level a cellulose membrane (pore size 0.2 $\mu$m), well adapted to the perimeter of the cartilage-bone junction of the defect area, was inserted. The remaining defect space was filled up to the surface level of the adjacent articular cartilage with a chondrogenic matrix composition as described in this application at page 15, lines 15-21; page 16, lines 7-11; and page 22, lines 1-17.

About ten weeks after the operation and treatment, the animals were killed and the knee joint components chemically fixed in buffered glutaraldehyde (4%) solutions containing 2.5% Cetyl pyridinium chloride. Following dehydration, in a graded series of increasing ethanol concentration, and embedding in methylmethacrylate, histologic sections were produced and stained with McNeil Tetrachrome and Toluidine Blue O in preparation for light microscopic examination.

That part of the defect space corresponding in level to the subchondral bone, i.e., where osteogenic matrix had been placed, was fully filled with newly-formed bone tissue. Likewise, the defect space adjacent to articular cartilage tissue, i.e., in the region above the cellulose membrane filled with the chondrogenic matrix composition, was filled with articular cartilage repair tissue.

I claim:

1. A mixture for the treatment of defects in bone comprising:
    a matrix or matrix-forming material used to fill a defect in bone;
    an angiogenic factor at an appropriate concentration contained within the matrix or matrix forming material to stimulate the formation and ingrowth of the blood vessels and associated cells in the matrix and the area of the defect; and
    an osteogenic factor associated with a delivery system, the delivery system being dissolved, suspended or emulsified in the matrix or matrix-forming material and the osteogenic factor being present at an appropriate concentration, for subsequent delivery to bone repair cells to promote the cells to develop into bone cells which form bone.

2. The mixture according to claim 1, wherein the angiogenic factor is selected from the group consisting of bFGF, a mixture of bFGF and heparin sulfate, TGF-$\beta$ PDGF-$\alpha$, angiogenin, angiotropin and combinations thereof.

3. The mixture according to claim 1, wherein the osteogenic factor is selected from the group consisting of TGF-$\beta$, a mixture of a TGF-$\beta$ and EGF, osteogenin, BMP and combinations thereof.

4. The mixture according to claim 1, wherein the matrix used to fill the defect area is selected from the group consisting of fibrin, collagen, gelatin, agarose, calcium phosphate containing compounds and combinations thereof.

5. The mixture according to claim 1, wherein the angiogenic factor is bFGF present at a concentration of 5-10 ng/ml in the matrix and the osteogenic factor is TGF-$\beta$ associated with the delivery system and at a concentration of 100 ng/ml in the matrix.

6. The mixture according to claim 5 further comprising an amount of heparin sulfate sufficient to enhance the angiogenic activity of the bFGF.

7. The mixture according to claim 1, wherein the delivery system is selected from the group consisting of liposomes, bioerodible polymers, collagen fibers chemically linked to heparin sulfate proteoglycans, carbohydrate-based corpuscles, and water-oil emulsions.

8. A method of inducing bone formation at a selected site in bone tissue of an animal in need of the treatment comprising filling the site with the mixture of claim 1.

9. A mixture for the treatment of defects in bone comprising:
    a collagenous matrix solution;
    basic FGF present at a concentration of 5-10 ng/ml of matrix solution; and
    TGF-$\beta$ encapsulated in liposomes for subsequent delivery to bone repair cells and present at a concentrations of 100 ng/ml of matrix solution.

10. A method of inducing bone formation at a selected site in bone tissue of an animal in need of the treatment comprising filling the site with the mixture of claim 9.

11. The mixture according to claim 9 further comprising an amount of heparin sulfate sufficient to enhance the angiogenic activity of the bFGF.

12. A method for treating a defect in bone in an animal in need of the treatment comprising:
    filling the defect with a matrix containing an effective amount of an angiogenic factor to stimulate formation and ingrowth of blood vessels and associated cells, and an effective amount of an osteogenic factor associated with a delivery system for subsequent delivery to bone repair cells to induce differentiation of the cells into mature bone tissue.

13. A method for treating a full-thickness defect in a joint in an animal in need of the treatment comprising:
    filling the bones portion of the full-thickness defect with a first matrix containing an effective amount of an angiogenic factor to stimulate formation and ingrowth of blood vessels with associated cells and containing an osteogenic factor associated with a delivery system that subsequently releases the osteogenic factor at a concentration sufficient to induce differentiation of bone repair cells into bone cells which form bone;

covering the matrix-filled bone portion of the full-thickness defect with a membrane, which prevents migration of cells from the bone defect side to the cartilage defect side;

sealing the membrane to the perimeter of the defect in the region of the cartilage-bone junction; and filling the cartilage portion of the full-thickness defect with a second matrix containing an effective amount of a proliferation agent to stimulate proliferation of repair cells, an effective amount of a chemotactic agent to attract repair cells, and an effective amount of a transforming factor associated with a delivery system that subsequently releases the transforming factor at a concentration sufficient to transform repair cell into chondrocytes.

14. The method according to claim 13 further comprising the step of covering the surface of the cartilage portion of the full-thickness defect with transglutaminase prior to dressing the defect or lesion with the second matrix.

15. The method of claim 13 wherein the osteogenic factor, the proliferation agent, and the transforming factor, are TGF-$\beta$.

16. The method according to claim 15, wherein the angiogenic factor is bFGF.

17. The method of claim 13 in which the delivery systems for the delivery of the transforming factor and the osteogenic factor are selected from the group consisting of liposomes, bioerodible polymers, collagen fibers chemically linked to heparin sulfate proteoglycans, carbohydrate-based corpuscles, and water-oil emulsions.

18. The method of claim 13 in which the first matrix is selected from the group consisting of fibrin, collagen, gelatin, agarose, calcium phosphate containing compounds and combinations thereof.

19. The method of claim 13 in which the first matrix is selected from the group consisting of fibrin, collagen, gelatin, agarose, and combinations thereof.

20. The method according to claim 13, wherein the first matrix and the second matrix are fibrin which is formed by addition of thrombin to a solution of fibrinogen immediately before filling the defect or lesion with the fibrinogen solution.

21. The method according to claim 13 wherein the angiogenic factor is bFGF at a concentration of 5-10 ng/ml of the first matrix;

the osteogenic factor is TGF-$\beta$ encapsulated in liposomes for subsequent delivery and present at a concentration of 100 ng/ml of the first biodegradable matrix;

the proliferation agent and the chemotactic agent are TGF-$\beta$ present at a concentration of 2-10 ng/ml of the second matrix; and the transforming factor is TGF-$\beta$ encapsulated in liposomes for subsequent delivery and present at a concentration of 200-2000 ng/ml of the second matrix.

22. The method according to claim 21, wherein the first matrix also contains an amount of heparin sulfate sufficient to enhance the angiogenic activity of the bFGF.

23. The method according to claim 13, wherein the first matrix and the second matrix further contain a cell adhesion promotion factor comprising the tripeptide Arg-Gly-Asp.

24. A method for treating a full-thickness defect in a joint of an animal in need of the treatment comprising:

filling the bone portion of the full-thickness defect with a first collagenous matrix containing bFGF at a concentration of 5-10 ng/ml of the first collagenous matrix, and containing TGF-$\beta$ in liposomes for subsequent delivery at a concentration of 100 ng/ml of the first collagenous matrix;

covering the first collagenous matrix-filled bone portion of the full-thickness defect with a membrane, which is impermeable to blood vessels and cells;

sealing the membrane at its perimeter to the edges of the defect in the region of the cartilage-bone junction; and filling the cartilage portion of the full-thickness defect with a second collagenous matrix containing TGF-$\beta$ at a concentration of 2-10 ng/ml of the second collagenous matrix, and containing TGF-$\beta$ in liposomes for subsequent delivery at a concentration of 200-2000 ng/ml of the second collagenous matrix.

25. The method according to claim 24 further comprising the step of covering the surface of the cartilage portion of the full-thickness defect with transglutaminase prior to filling the defect with the second collagenous matrix.

26. The method according to claim 24, wherein the first collagenous matrix also contains an amount of heparin sulfate sufficient to enhance the angiogenic activity of the bFGF.

* * * * *

UNITED STATES PATENT AND TRADEMARK OFFICE
CERTIFICATE OF CORRECTION

PATENT NO. : 5,270,300          PAGE 1 OF 2
DATED : December 14, 1993
INVENTOR(S) : Hunzinker, E.

It is certified that error appears in the above-identified patent and that said Letters Patent is hereby corrected as shown below:

ITEM [56] REFERENCES CITED:
Page 3, OTHER PUBLICATIONS

Col. 1, line 8, "351" should be --251--;

line 19, "Ary" should be --Arg--.

Col. 2, line 16, Delete second occurrence of "Natl.".

Col. 2, line 56, "supa" should be --supra--;

line 66, "226771" should be --2267-71--.

Col. 12, line 38, "65(22)" should be --265(22)--;

line 57, "fullthickness" should be --full-thickness--.

Col. 16, lines 40-41, "concentrations" should be --concentration--.

Col. 17, line 37, After "agarose," insert --and--;

line 38, Delete "and" and insert therefor --or--;

UNITED STATES PATENT AND TRADEMARK OFFICE
CERTIFICATE OF CORRECTION

PATENT NO. : 5,270,300

DATED : December 14, 1993

INVENTOR(S) : Hunzinker, E.

It is certified that error appears in the above-indentified patent and that said Letters Patent is hereby corrected as shown below:

Col. 17, line 39, Delete "first" and insert therefor --second--.

Signed and Sealed this

Twentieth Day of September, 1994

Attest:

BRUCE LEHMAN

Attesting Officer   Commissioner of Patents and Trademarks